United States Patent
Hoffman et al.

(10) Patent No.: US 6,389,096 B1
(45) Date of Patent: May 14, 2002

(54) METHODS AND APPARATUS FOR PROVIDING ADDITIONAL COMPUTED TOMOGRAPHY IMAGING MODES

(75) Inventors: David M. Hoffman, New Berlin; Robert F. Senzig, Germantown; Stanley H. Fox, Brookfield, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/721,330

(22) Filed: Nov. 22, 2000

(51) Int. Cl.[7] .................................................. A61B 6/03
(52) U.S. Cl. ............................................. 378/19; 378/4
(58) Field of Search ............................. 378/4, 8, 19, 99

(56) References Cited

U.S. PATENT DOCUMENTS 6,292,919 B1 * 7/2001 Fries et al. ................. 714/758

6,272,201 B1 * 8/2001 Pan ............................... 378/19

OTHER PUBLICATIONS

Toshiba America Medical Systems, "Aquilion™ multi–slice CT," http://toshiba.com/tams/newtams/ct/ctset.html, one page available on the World Wide Web on Nov. 12, 2000.

* cited by examiner

Primary Examiner—David V. Bruce
(74) Attorney, Agent, or Firm—Carl B. Horton, Esq.; Armstrong Teasdale LLP

(57) ABSTRACT

In one aspect, the invention is a method for changing at least one of a number of image slices and in-plane resolutions available in an existing imaging system. The method includes steps of: replacing the existing detector array with a replacement detector array having either narrower detector cells in the x-direction than an existing detector array, a greater number of detector cells than that of the existing detector array, or both; and selecting an in-plane resolution of the replacement detector array in accordance with a maximum bandwidth limit of a communication path in the imaging system.

18 Claims, 7 Drawing Sheets

METHODS AND APPARATUS FOR PROVIDING ADDITIONAL COMPUTED TOMOGRAPHY IMAGING MODES

BACKGROUND OF THE INVENTION

This invention relates generally to methods and apparatus for providing increased resolution and/or additional imaging slices for computed tomography imaging systems, and especially to methods and apparatus for upgrading resolution and/or imaging slices coverage of existing computed tomographic imaging systems.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

The axis of rotation of the rotating gantry on which the detector and x-ray source rotate is referred to as a z-axis. The detector array is considered as having a z-direction defined as a direction parallel to the z-axis of the rotating gantry. When a patient is scanned, the z-direction of the detector array is usually at least approximately aligned with the patient's spine.

A single-slice detector array is used in at least one known CT imaging system. Referring to the representation of a portion of a single slice detector array 18 of FIG. 3, only one detector row extends in a direction transverse to the z-direction. At least one other known CT imaging system utilizes a multi-slice detector array having more than one row, for example, four rows or sixteen rows, each row extending in a direction transverse to the z-direction. The CT imaging systems referred to here have detectors arrays in which the rows are arranged in one or more arcs transverse to the z-axis. It is thus convenient to define an x-direction as a direction along the arc of the detector. Detectors are often represented by flat, two-dimensional projections of their target surfaces, with one dimension representing the z-direction and the other dimension representing the x-direction. This convention is used in many of the figures in this description.

In known CT imaging systems utilizing the embodiment of prior art detector array 18 of FIG. 3, the data acquisition system and detector array of the prior art imaging system do not provide a trade-off between resolution and number of slices. In all cases, exactly one slice of data is received from the detector at a time. Some additional flexibility is provided in another known imaging system that utilizes a multislice detector having rows not all having the same thickness in the z-direction. However, the bandwidth of the data acquisition system in this system is able to process no more than a fixed maximum number of slices that is less than the number of rows of detector elements 20 in detector array 18. For example, in imaging systems having sixteen row detector arrays, only four slices of attenuation data can be acquired at one time. When using more than four rows of detector elements 20, the outputs of detector elements 20 in selected adjoining rows of detector array 18 are combined in the z-direction to keep the number of slices, and hence, the data bandwidth of the imaging system at or below its maximum limit.

It would thus be desirable to provide existing clinical computed tomography (CT) imaging with enhanced productivity and new applications by increasing the range of imaging combinations available. True isotropic and/or high-resolution volumetric scanning, for example, would enable new cardiac, interventional and screening applications as well as improved image quality for at least heads and inner ears with an increased productivity.

BRIEF SUMMARY OF THE INVENTION

There is thus provided, in one embodiment of the present invention, a method for changing a number of image slices and/or in-plane resolutions available in an existing imaging system having a radiation source, an existing detector array having an x-direction and a z-direction and configured to acquire attenuation measurements of an object between the radiation source and the existing detector array, an image reconstructor configured to reconstruct an image of the object from attenuation data, and a communication path between the existing detector array and the image reconstructor; the communication path including a data acquisition system coupled between the existing detector array and the imaging reconstructor, the communication path also having a maximum bandwidth limit. The method includes steps of: replacing the existing detector array with a replacement detector array having either narrower detector cells in the x-direction than the existing detector array, a greater number of detector cells than that of the existing detector array, or both; and selecting an in-plane resolution of the replacement detector array in accordance with the maximum bandwidth limit of the communication path.

Isotropic and/or high resolution volumetric scanning is achieved in embodiments of the present invention by using replacement detectors capable of imaging a larger number of slices and/or having higher resolution in the x- and/or z-direction.

DETAILED DESCRIPTION OF THE INVENTION

Figure 1:
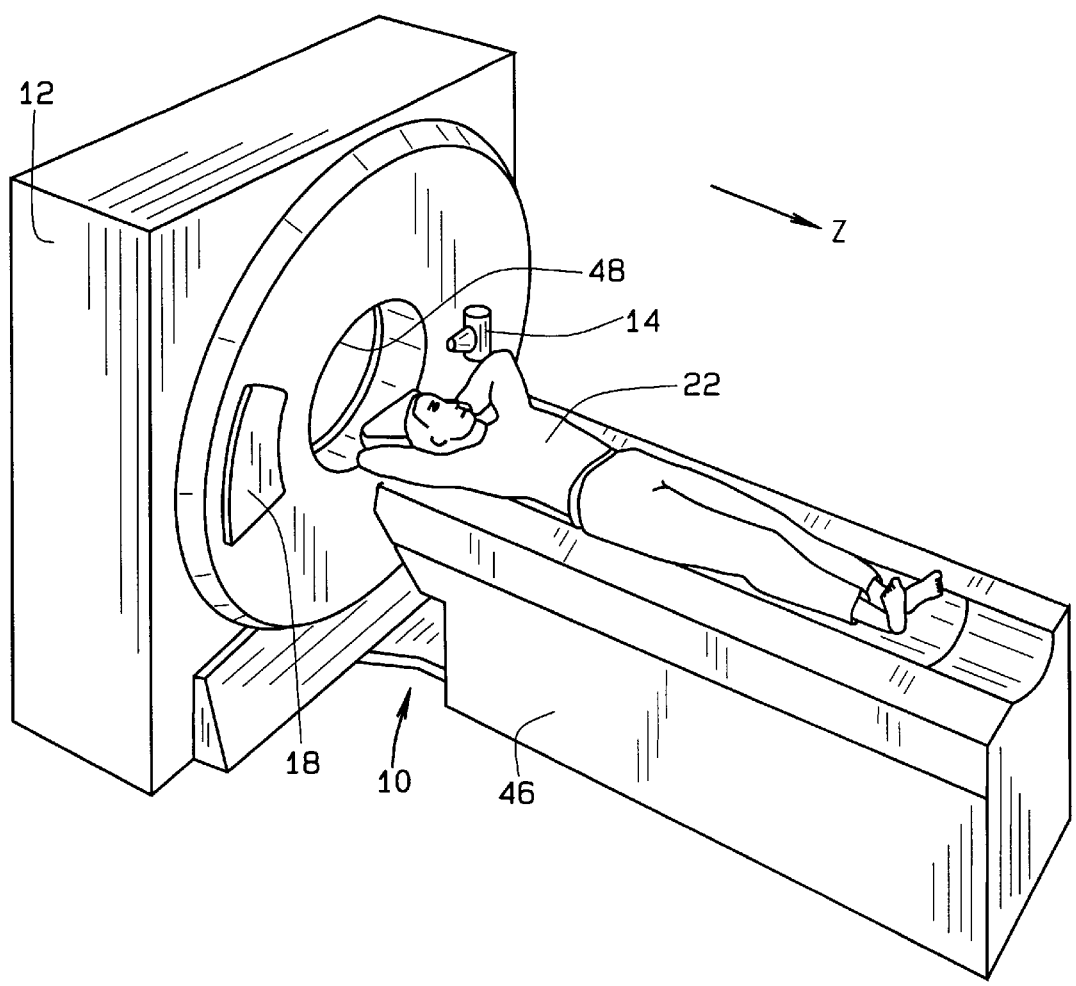
FIG. 1 is a pictorial view of a CT imaging system.
Figure 2:
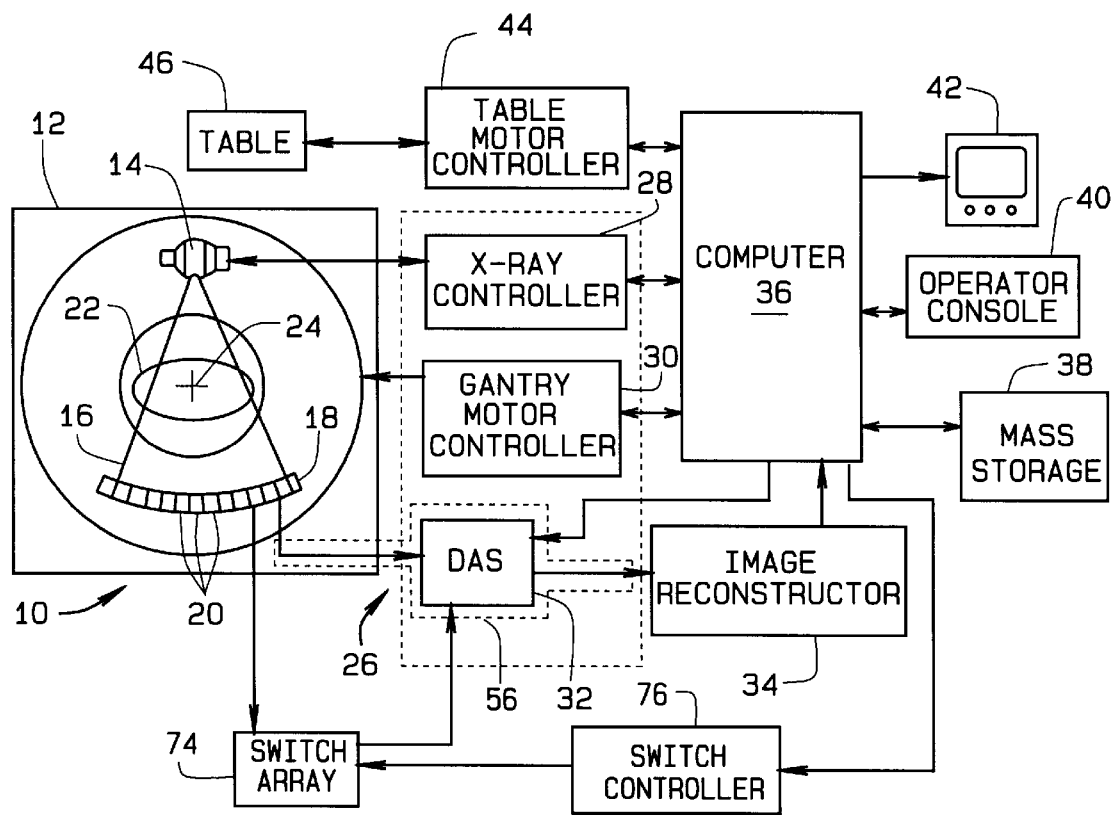
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 is a discrete element of detector array 18 that produces an electrical signal representing the intensity of an impinging x-ray beam. In a CT imaging system 10, detector elements 20 do not correspond to particular pixel elements of images. However, detector elements 20 have one property similar to pixel elements; namely, detector elements 20 of detector array 18 are not further divisible to produce additional independent electrical signals.

(Switch array 74 and switch controller 76 are not present in all embodiments of existing imaging systems 10. Because they are added in some embodiments of the invention, they are shown separately in FIG. 2.)

As the x-ray beam passes through a patient 22, the bean is attenuated. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. The axis of rotation of gantry 12 defines a z-axis that is usually at least approximately parallel to the spine of a patient 22 being imaged.

Figure 3:
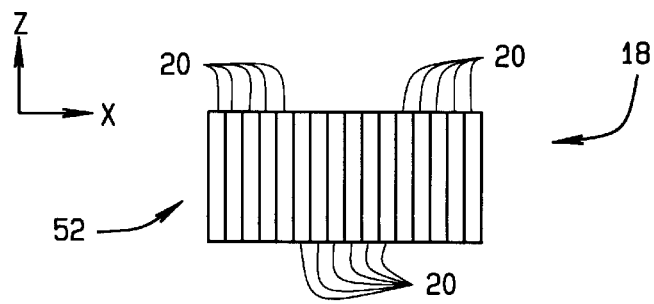
FIG. 3 is a two-dimensional representation of a portion of a prior art single slice detector.
Figure 4:
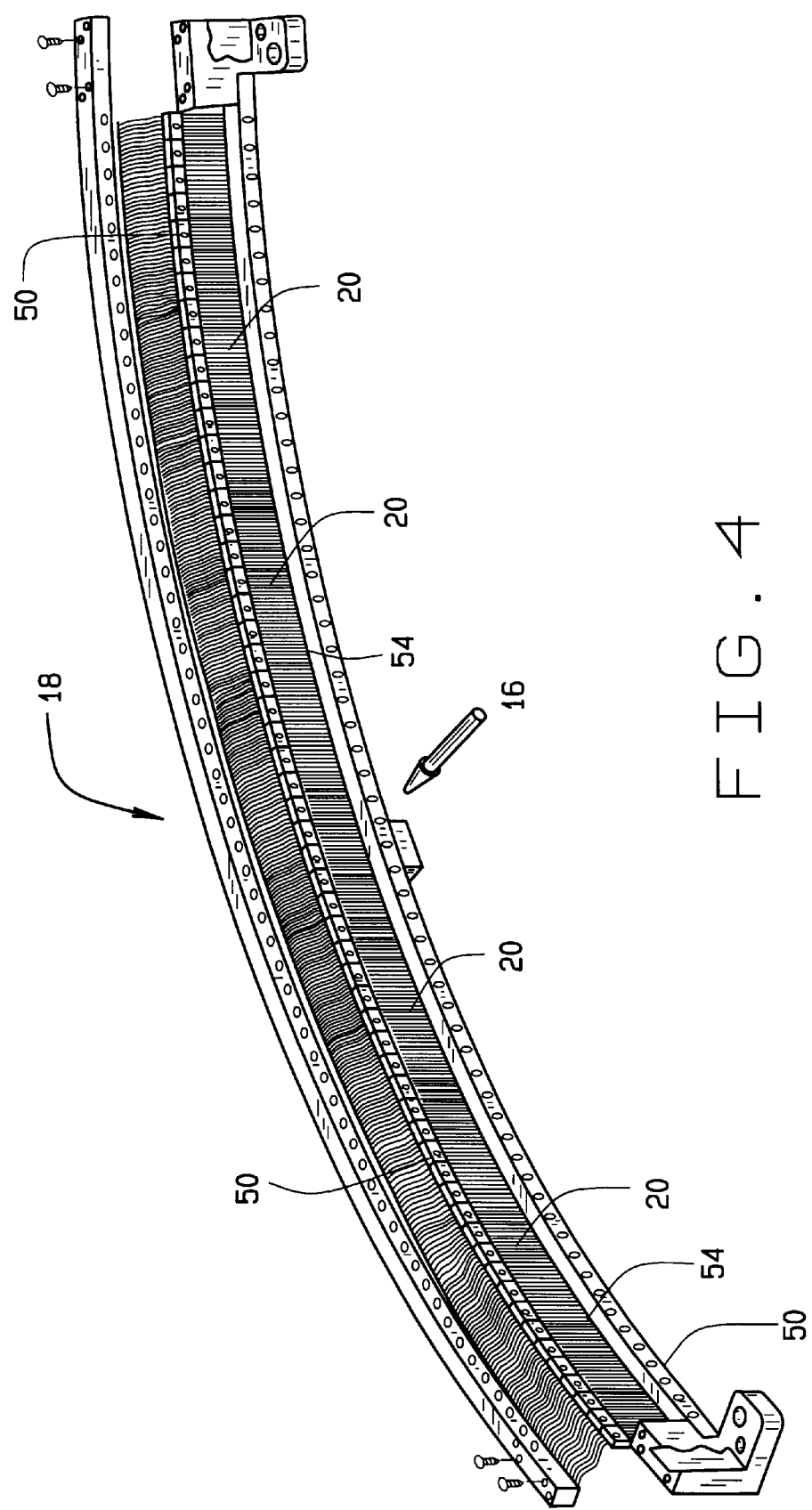
FIG. 4 is a perspective drawing of a detector array illustrating its curvature.

In an existing CT imaging system 10, detector array 18 may be either a single slice detector having only one row of detector elements as illustrated in FIGS. 1 and 2, or a multi-slice array having a plurality of detector elements. In either case, and referring to FIG. 4, detector array 18 typically includes or is secured to an arc-shaped detector housing 50. In accordance with the convention described above, in some figures, such as FIGS. 3 and 5, detector arrays such as array 18 are represented as a flat projection 52 of a top surface 54 of the array, i.e., a surface that faces radiation source 14.

Images reconstructed by imaging system 10 represent one or more "slices" of a volume of patient 22. Dimensions in the z-direction are called thicknesses, because such dimensions correspond to a thickness of the volume of patient 22 contributing to the slice image or images.

An "in-plane" resolution of detector array 18 is defined as a resolution limit of attenuation measurements in the x-direction. A detector array 18 has a maximum in-plane resolution that is achieved only when attenuation data from each detector element 20 of a row of detector array 18 that corresponds to an image slice in question is separately acquired by DAS 32. When a multi-slice detector array is used, outputs of detector elements 20 in adjacent rows of detector array 18 can be combined in the z-direction to produce a slice or slices representing a selected thickness slice of a volume of patient 22. Combining detector elements 20 in the z-direction does not affect in-plane resolution. Having narrower detector elements 20 (i.e., detector elements having lesser extent in the x-direction) increases in-plane resolution.

A communication path 56 is provided between detector 18 and image reconstructor 34. Communication path 56 includes DAS 32, and is limited by one or more of the number of communication signal lines from detector array 18 to DAS 32, a processing capability of DAS 32, and a signal bandwidth (measured, for example, in bytes per second) from DAS 32 to image reconstructor 34. This maximum limit of communication path 56 is referred to as the maximum bandwidth limit, or maximum data bandwidth.

Figure 5:
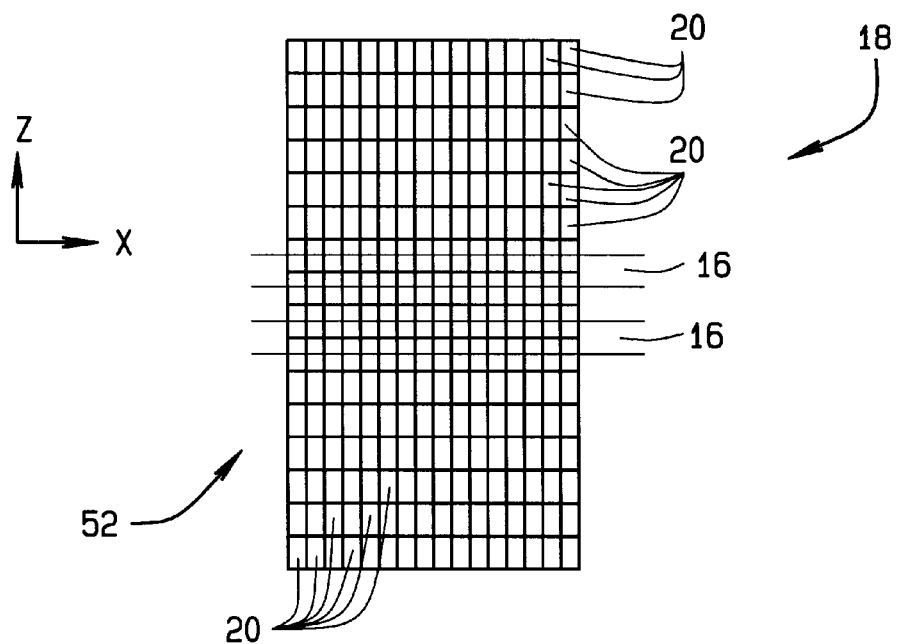
FIG. 5 is a two-dimensional representation of a portion of a multi slice detector array.

In one embodiment and referring to FIGS. 1, 2, and 5, a multislice imaging system utilizes a 16-row detector array 18 in conjunction with a data acquisition system 32 having sufficient hardware to process four slices at a time. A split dual-slit tube collimator or a post-patient collimator (not shown) is used to provide slices of selected thickness less than a thickness of a detector array 18 row. For example, an adjustable dual-slit collimator produces two x-ray beams 16, each of which straddles a row boundary of detector array 18. Each of the pair of attenuated beams 16 impinges only a portion of the two rows adjacent the corresponding row boundary. Attenuation data sufficient to reconstruct four image slices is thus obtained, each slice representing a thickness less than that of a corresponding detector array 18 row from which data is obtained. In another embodiment, each of the pair of attenuated beams 16 impinges separate groups of detector rows, with rows at the edges of beams 16 not necessarily fully impinged.

Figure 6:
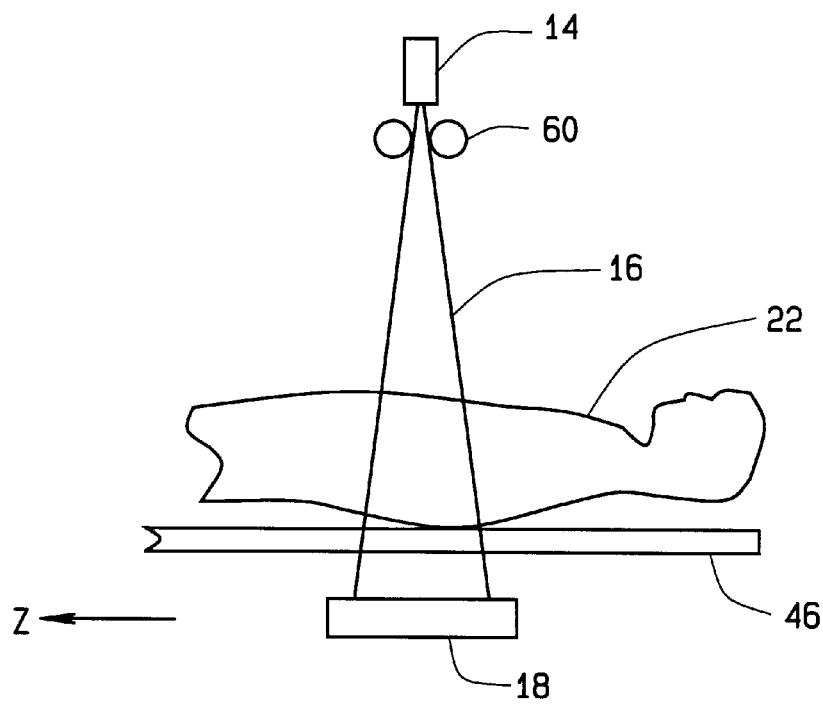
FIG. 6 is a schematic cross-sectional view of a portion of an imaging system, showing an added, adjustable pre-patient collimator configured to adjust a thickness of a radiation beam. (The thickness of the radiation beam and of the detector in the z-direction is greatly exaggerated for clarity.)

Referring to FIG. 6, flexibility in selecting slice widths of reconstructed images is obtained by providing imaging system 10 with an adjustable collimator 60. Adjustable collimator 60 is, for example, a pre-patient collimator configured to control a thickness of radiation beam 16 impinging on detector array 18, or a post-patient collimator similarly configured.

Figure 7:
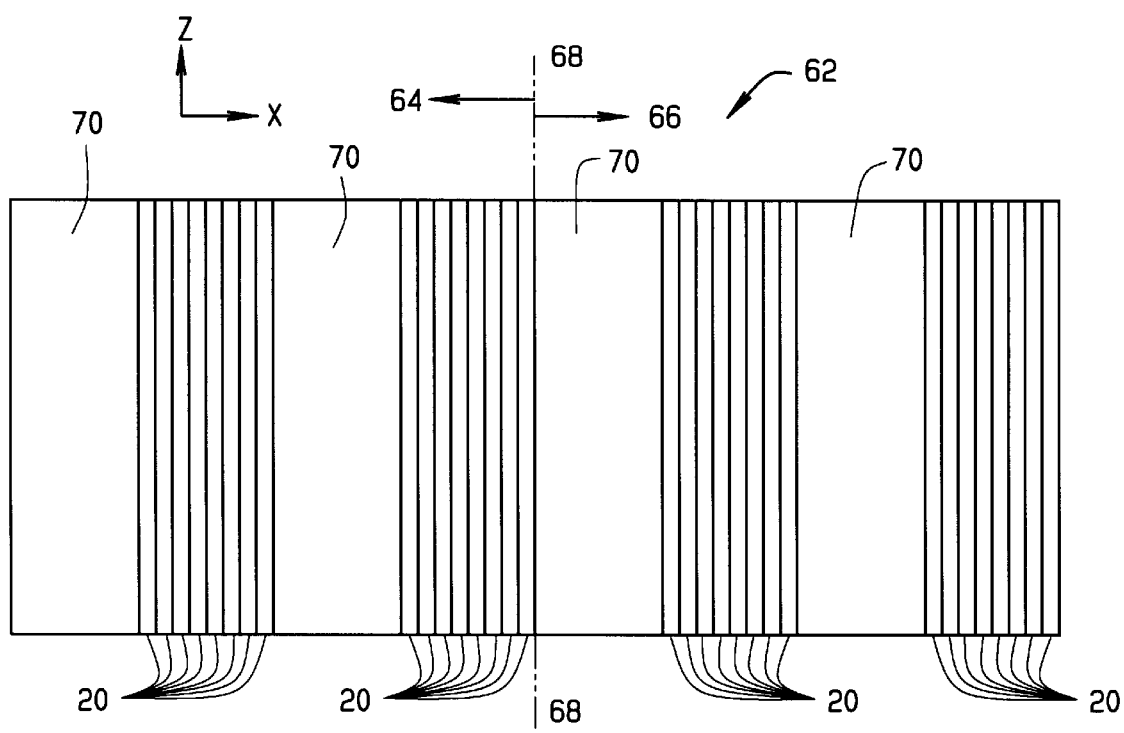
FIG. 7 is a two dimensional representation of a portion of a replacement detector array embodiment of the present invention in which only complementary detector elements across a centerline of the replacement detector array are provided.

In another embodiment of the present invention and referring to FIG. 7, an existing single row detector array 18 is replaced by a single-row replacement detector array 62 having narrower detector elements 20 in the x-direction than existing detector array 18, which it replaces. For purposes of discussion, the x-direction of replacement detector array 62 is considered as being divided into a left half 64 and a right half 66. (The terminology "left" and "right" is arbitrary, but shall be used consistently throughout this explanation.) Higher resolution is achieved without exceeding the maximum bandwidth limit of communication path 56 by acquiring data from detector elements 20 in a "complementary relationship" in left half 64 and right half 66 of replacement detector array 62. Detector elements 20 are said to have a "complementary relationship" with one another if, for each detector element 20 in left half 64 from which attenuation measurements are individually acquired, there exists a corresponding detector element 20 in right half 66 the same distance from a center 68 of detector array 62 from which attenuation measurements are not acquired during a scan, and vice versa. (Center 68 of detector array 62 is at the division between left half 64 and right half 66.) By acquiring attenuation data from complementary detector elements 20, attenuation data constituting a full sample of a slice is obtained in a 360 degree rotation of gantry 12.

In one embodiment in which a fixed in-plane resolution is selected in advance, detector elements 20 are not provided in positions 70 of replacement detector array 62 where such positions are in a complementary relationship with detector elements 20 that are used for acquisition of attenuation data. In this embodiment, replacement detector array 62 has no more detector elements 20 than does existing detector array 18.

Figure 8:
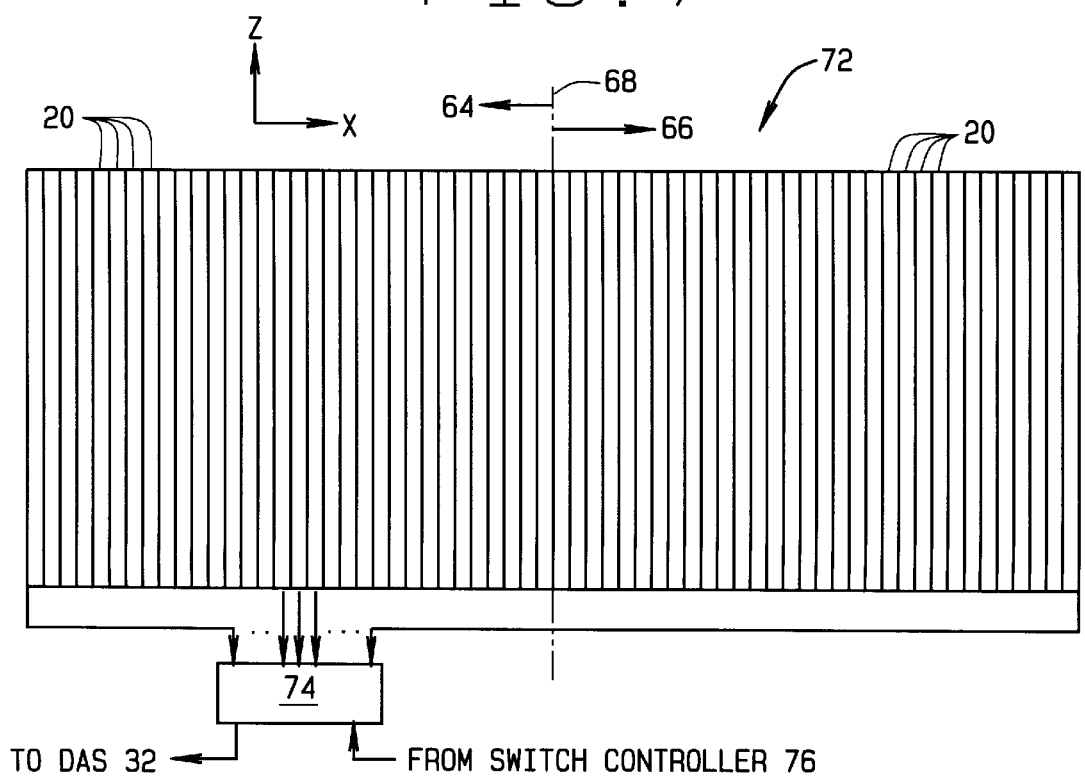
FIG. 8 is a two-dimensional representation of a portion of a replacement detector array embodiment of the present invention in which complementary detector elements across a centerline of the replacement detector array are switched using a switch array.

In another embodiment and referring to FIG. 8, detector elements 20 are provided in all positions of a replacement detector array 72. A switch array 74 and switch controller 76 are also added to imaging system 10. Switch array 74 is, for example, a field effect transistor (FET) array that is physically part of replacement detector array 72. When enhanced resolution is needed, attenuation measurement from half of the narrow detector elements 20 of left half 64 of replacement detector array 62 are acquired, and attenuation measurements from a complementary selection of detector elements 20 of right half 66 are also acquired. When enhanced resolution is not required, switch controller 76 controls switch array 74 to adjust the in-plane resolution of replacement detector array 72 by grouping selected outputs of detector elements 20 in the x-direction. The charges from the groups of detector elements 20 are thus added together, reducing the number of attenuation measurements that are acquired so that the maximum bandwidth of communication path 56 is not exceeded.

Figure 9:
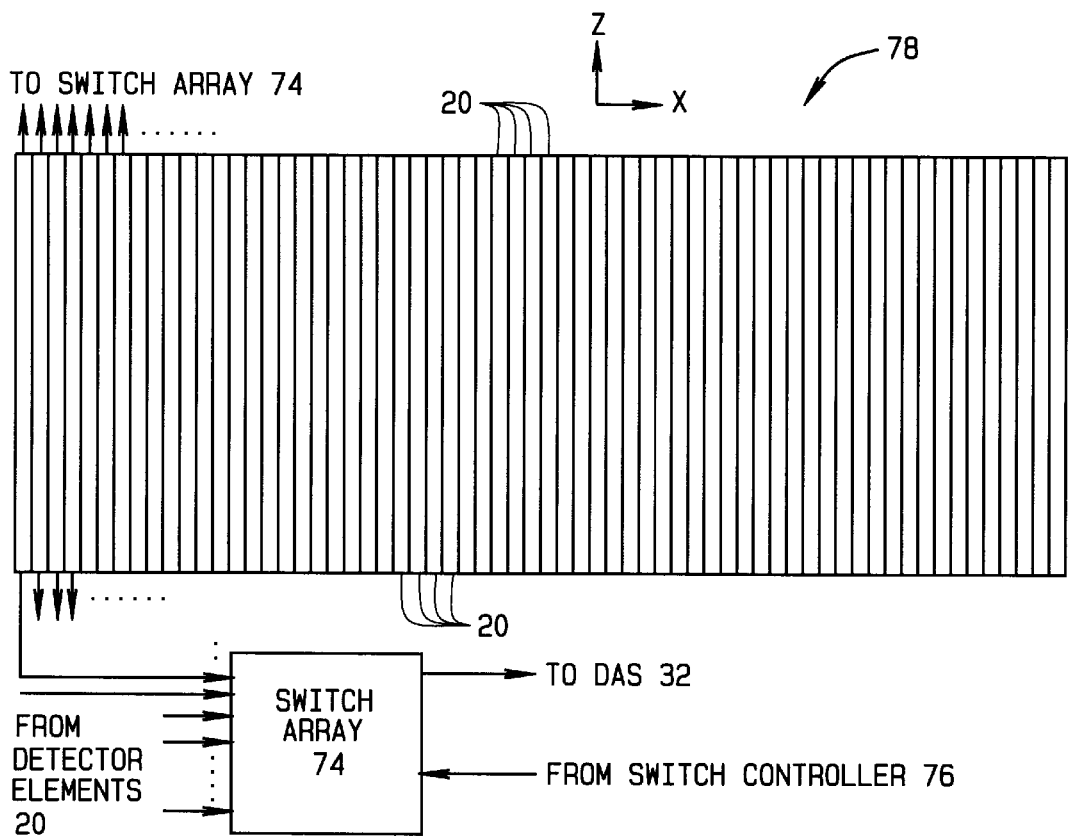
FIG. 9 is a two-dimensional representation of a portion of a replacement detector array having more rows than the existing detector array that it replaces, and as many or a greater number of detector elements in the x-direction.

In yet another embodiment of the present invention and referring to FIG. 9, a replacement detector array 78 is provided that has more rows of detector elements 20 than existing detector array 18, which it replaces. Replacement detector array 78 also has either the same or more numerous detector elements 20 in the x-direction than existing detector array 18. For example, detector array 78 has narrower detector elements in each row than those of existing detector array 18. In one exemplary embodiment, existing detector array 18 has one row of detector elements, and replacement detector array 78 has two rows. A switch array 74 and a switch controller 76 configured to selectively combine outputs of detector elements 20 of replacement detector array 78 are also added to imaging system 10. Both an in-plane resolution and a number of slices are selected so that the maximum bandwidth of communication path 56 is not exceeded by the attenuation data, and switch controller 76 and switch array 74 are operated to adjust at least the in-plane resolution of replacement detector array 78. In one embodiment, the in-plane resolution of replacement detector array 78 is adjusted by selectively combining outputs of detector elements 20 in the x-direction. In another embodiment, switch controller 76 and switch array 74 are also configured to selectively combine outputs of detector elements 20 in the x-direction and/or the z-direction, to simultaneously select a thickness and/or number of reconstructed image slices and an in-plane resolution within limitations set by the maximum bandwidth limit of communication path 56. In another embodiment, an adjustable collimator 60 of a type already described is used to adjust a thickness of and/or a number of slices of image data to be processed.

Figure 10:
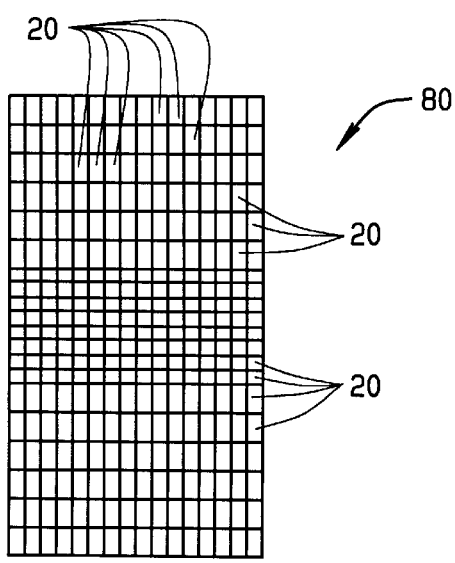
FIG. 10 is a two-dimensional representation of a portion of a multi-slice replacement detector array having rows of detector elements, not all of which are the same thickness in the z-direction.

In other embodiments of the present invention, a multi-row replacement detector array 80 is provided that includes rows that do not all have the same thickness in the z-direction, as illustrated in FIG. 10. By combining cells in the x-direction (thereby adjusting in-plane resolution) and/or the z-direction (thereby adjusting a number of image slices and/or slice thicknesses), additional flexibility is provided for the selection of in-plane resolution and number of slices within the maximum bandwidth limitation of communication path 56. Still more flexibility is provided in those embodiments in which an adjustable collimator 60 and/or a greater number of detector elements 20 in the x-direction are provided. These and other embodiments of the present invention are useful in providing better and more flexible imaging coverage for specific body parts such as heads, inner ears, and hearts.

Figure 11:
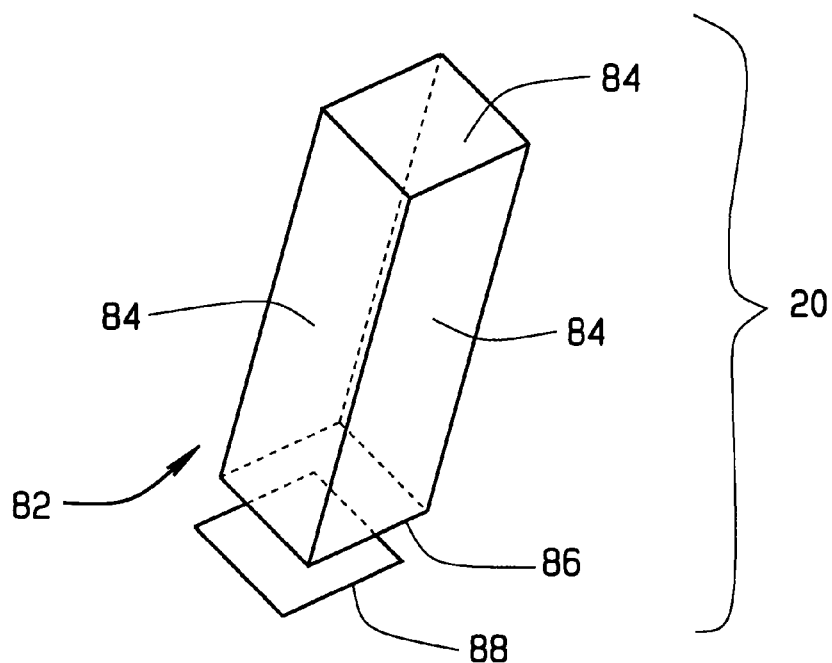
FIG. 11 is a perspective view of a single detector element (with some hidden surfaces illustrated), showing surfaces of a scintillator that can advantageously be covered by a thin, low damage reflector in embodiments of the present invention.

Detector arrays 18 having thin, low damage reflectors can be used advantageously in embodiments of the present invention. For example, OPTICLAD™ reflectors can be used. (OPTICLAD™ is a trademark of General Electric Medical Systems, Inc., Milwaukee, Wis.) OPTICLAD reflectors are polyester-based sheets having a gold or silver coating and a pressure-sensitive adhesive coating doped with titanium dioxide. Referring to FIG. 11, in one embodiment, detector elements 20 comprise scintillator elements 82 wrapped in OPTICLAD reflector material 84 on all sides except a side 86 that is optically coupled to a photodetector element 88.

Figure 12:
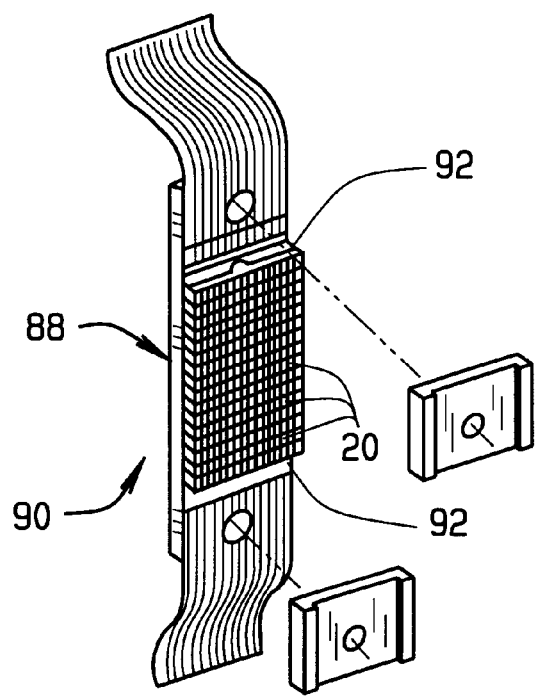
FIG. 12 is a drawing of a detector module of a multi-slice detector array of the present invention, the detector module comprising a multi-row array of detector elements.

In one embodiment and referring to FIG. 12, detector elements 20 are provided in modules 90 that comprise a plurality of detector elements 20. Each module 90 has its own set or sets of switching elements 92, for example, arrays of FETs (field effect transistors). Modules 90 are assembled into detector housing 50. Switch array 74 in such embodiments comprises a set of all of switching elements 92 of all modules 90 assembled in detector housing 50.

It will thus be recognized that embodiments of the present invention can be used to enhance the detector coverage of the installed base of CT imaging systems by providing greater flexibility in selecting a number of slices to image, and by increasing resolution in either or both of the X and Z directions by providing smaller detector element sizes and higher resolution. These improvements are provided without the need to increase the maximum bandwidth of communication paths in the existing CT imaging systems. Those skilled in the art will also recognize that the invention is not limited to upgrades of existing CT imaging systems. For example, originally manufactured imaging systems equivalent to the upgraded systems described here are useful in their own right and provide the advantages discussed herein.

While the invention has been described in terms of various specific embodiments, those skilled in the art will recognize that the invention can be practiced with modification within the spirit and scope of the claims.

What is claimed is:

1. A method for changing at least one of a number of image slices and in-plane resolutions available in an existing imaging system having a radiation source, an existing detector array having an x-direction and a z-direction and configured to acquire attenuation measurements of an object between the radiation source and the existing detector array, an image reconstructor configured to reconstruct an image of the object from attenuation data, and a communication path between the existing detector array and the image reconstructor;

the communication path comprising a data acquisition system coupled between the existing detector array and the imaging reconstructor, the communication path also having a maximum bandwidth limit;

said method comprising the steps of:

replacing the existing detector array with a replacement detector array having at least one of narrower detector cells in the x-direction than the existing detector array and a greater number of detector cells than that of the existing detector array; and selecting an in-plane resolution of the replacement detector array in accordance with the maximum bandwidth limit of the communication path.

2. A method in accordance with claim 1 wherein said step of selecting an in-plane resolution of the replacement detector array is performed prior to said step of replacing the existing detector array, and the replacement detector array has a fixed in-plane resolution.

3. A method in accordance with claim 2 wherein the imaging system has a rotating gantry on which the radiation source and detector array are mounted, the replacement detector array has a left half and a right half in the x-direction and a greater number of detector cells in the x-direction than the existing detector array, and said method further comprises the step of acquiring data from detector cells in complementary relationships in a left half and a right half of the replacement detector array.

4. A method in accordance with claim 1 wherein the replacement detector array further comprises a switch configured to adjust an in-plane resolution of the replacement detector array, said method further comprising the step of providing the imaging system with a switch controller configured to control the switch to adjust the in-plane resolution in accordance with the selected in-plane resolution.

5. A method in accordance with claim 4 wherein the replacement detector array has a number of rows in the z-direction greater than that of the existing detector array, and further wherein said step of selecting an in-plane resolution of the replacement detector array in accordance with the maximum bandwidth limit of the communication path comprises the step of selecting both an in-plane resolution of the replacement detector array and a number of slices for imaging in accordance with the maximum bandwidth limit of the communication path.

6. A method in accordance with claim 5 wherein said step of selecting both an in-plane resolution and a number of slices for imaging comprises the step of selecting a number of slices for imaging greater than a number of rows of detector elements of the replaced detector array.

7. A method in accordance with claim 6 further comprising the step of providing the imaging system with an adjustable collimator configured to adjust a thickness of at least one radiation beam impinging on the replacement detector array, wherein said step of selecting a number of slices for imaging comprises the step of adjusting the adjustable collimator.

8. A method in accordance with claim 4 wherein the imaging system has a rotating gantry on which the radiation source and detector array are mounted, the replacement detector array has a left half and a right half in the x-direction, and said method further comprises the step of acquiring data from detector cells in complementary relationships in the left half and the right half of the replacement detector array.

9. A method in accordance with claim 1 further comprising the step of supplying the imaging system with an adjustable collimator configured to adjust a thickness of at least one radiation beam from the radiation source in the z-direction, and wherein the replacement detector array has narrower cells in the x-direction than the existing detector array.

10. A method in accordance with claim 1 wherein the replacement detector array has a plurality of rows of detector elements, not all of the rows having the same thickness in the z-direction.

11. A computed tomographic (CT) imaging system comprising:

a radiation source;

a detector array having an x-direction, a z-direction, and an adjustable in-plane resolution, said detector array configured to acquire attenuation measurements of an object between said radiation source and said detector array;

a data acquisition system configured to acquire said attenuation measurements from said detector array;

an image reconstructor configured to reconstruct an image of the object from attenuation data; and a communication path between said detector array and said image reconstructor, said communication path including a data acquisition system coupled between said detector array and said image reconstructor, said communication path having a maximum bandwidth limit for communicating said attenuation data.

12. A CT imaging system in accordance with claim 11 further comprising a switch configured to adjust the in-plane resolution of said detector array.

13. A CT imaging system in accordance with claim 12 wherein said detector array comprises a plurality of rows of detector elements, and said CT imaging system is configured to select a number of slices for imaging and an in-plane resolution of said detector array in accordance with the maximum bandwidth limit of said communication path.

14. A CT imaging system in accordance with claim 13 configured to selectively combine outputs of said detector elements in the x-direction and in the z-direction, depending upon a number and thickness of slices selected for imaging and the maximum bandwidth limit of said communication path.

15. A CT imaging system in accordance with claim 11 further comprising an adjustable collimator configured to control a thickness of a radiation beam impinging on said detector array.

16. A CT imaging system in accordance with claim 11 wherein said detector array has a left half and a right half in the x-direction, and wherein said CT imaging system is configured to acquire data from detector cells of said detector array in complementary relationships in the left half and the right half of said detector array.

17. A CT imaging system in accordance with claim 11 wherein said detector array is a multirow detector array, and further comprising an adjustable collimator configured to adjust a thickness of at least one radiation beam from said radiation source in the z-direction.

18. A CT imaging system in accordance with claim 17 wherein said detector array is a multirow detector array, and not all of the rows of said multirow detector array have the same thickness in the z-direction.

* * * * *